(12) United States Patent
Geisel (10) Patent No.: US 7,922,713 B2
(45) Date of Patent: Apr. 12, 2011

(54) HIGH EFFICIENCY, PRECISION ELECTROSURGICAL APPARATUS AND METHOD

(76) Inventor: Donald J. Geisel, Clifton Park, NY (US)

( * ) Notice: Subject to any disclaimer, the term of this patent is extended or adjusted under 35 U.S.C. 154(b) by 1174 days.

(21) Appl. No.: 11/552,581

(22) Filed: Oct. 25, 2006

(65) Prior Publication Data

US 2007/0156137 A1    Jul. 5, 2007

Related U.S. Application Data

(60) Provisional application No. 60/755,900, filed on Jan. 3, 2006.

(51) Int. Cl.
*A61B 18/04* (2006.01)
*A61B 18/14* (2006.01)
(52) U.S. Cl. ............... 606/29; 606/37; 606/45; 606/49
(58) Field of Classification Search .................. 606/29, 606/34, 37–40, 45, 49
See application file for complete search history.

(56) References Cited

U.S. PATENT DOCUMENTS

| 4,196,734 A | 4/1980 | Harris |
| 5,807,392 A | 9/1998 | Eggers |

*Primary Examiner* — Lee S Cohen
(74) *Attorney, Agent, or Firm* — Schmeiser, Olsen & Watts, LLP (57) ABSTRACT

An electrosurgical apparatus for cutting and/or coagulating living tissue, a method of forming the electrosurgical apparatus, and a method of using the electrosurgical apparatus. The cutting and/or coagulating living tissue is performed with one or two heated loops of resistance wire accompanied by sufficient electrical current across the living tissue to enable said cutting and/or coagulating to be performed. The electrosurgical apparatus may include: a glow blade having one or two glow loops of resistance wire; a radio frequency (RF) generator; and one or two voltage supplies configured to operate concurrently, while the one or two glow loops are heated to said glow, to supply both sufficient RF power and associated electrical current across the living tissue for cutting and/or coagulating the living tissue by the one or two glow loops. A first output of the RF generator is electrically coupled to the one or two glow loops.

32 Claims, 7 Drawing Sheets

HIGH EFFICIENCY, PRECISION ELECTROSURGICAL APPARATUS AND METHOD

RELATED APPLICATION

This present invention claims priority to U.S. Provisional Application No. 60/755,900, filed Jan. 3, 2006 and entitled "High efficiency, precision electrosurgical apparatus and method" and is incorporated herein by reference in its entirety.

FIELD OF THE INVENTION

The present invention relates to an electrosurgical apparatus for cutting and/or coagulating living tissue, a method of forming the electrosurgical apparatus, and methods of using the electrosurgical apparatus.

BACKGROUND OF THE INVENTION

Conventional electrosurgical devices are widely employed by surgeons for cutting and/or coagulating human tissue in operating rooms. They are used in lieu of a conventional blade or knife in situations where bleeding tissue can cause unwanted loss of blood. The basic electrosurgical device consists of a intermediate frequency RF generator with power capability on the order of several hundred watts, driven by approximately 1000 volts or higher. The generator common is connected to a patient pad, upon which a patient lies. The hot lead of the generator is connected via an insulating cable to a conductive shaped end for tissue cutting, called the cutting probe. The shape, for example, could be needle like, circular or flat. It is this conductive end which is employed for tissue cutting. When the conductive end of the generator hot lead is placed in contact with the patent, current flows through the patient to the patient pad. Since the current density is extremely high at the cutting probe, tissue is cut by burning and vaporization.

As tissue is cut, substantial smoke is generated with carbon and debris collecting on the cutting probe and along the cutting path through tissue. The destroyed tissue suffers trauma and healing is prolonged and accompanied by internal scaring. The currents than the generator must always flow from the cutting probe through the patient. Depending on the region of cutting, unwanted currents will flow via the path of least resistance to the patient pad. These currents could flow through sensitive organs, causing irreparable damage. High voltage is essential for the conventional electrosurgical unit to function. This level of energy is hazardous to both patient and surgeon. The precision of cutting by an electrosurgical approach does not compare with a conventional blade because a substantial amount of tissue is actually destroyed during cutting.

With the conventional electrosurgical unit, high voltage is necessary to initiate and maintain a current path from the cutting probe to target tissue, which is a form of ionization at room temperatures and pressure.

Moreover, it is stated in the Internet website whose address is a concateneation of "http://" and "www.usaccc.org/research/Hemotosis.jsp" that "[e]ighty to ninety percent of combat-related deaths occur within 1 hour of wounding. Fifty percent or more are attributable to uncontrolled bleeding. Recent evidence suggests that the majority of deaths due to hemorrhage in potentially survivable casualties involved non-compressible hemorrhages or were areas not conducive to a tourniquet. Currently, there is no ability to control non-compressible hemorrhage in casualties with clotting deficiencies short of immediate surgery."

Thus, there is a need for an electrosurgical device that overcomes at least one of the aforementioned disadvantages of conventional electrosurgical devices.

SUMMARY OF INVENTION

The present invention provides an electrosurgical apparatus for cutting and/or coagulating living tissue, comprising:

a glow blade having one or two glow loops, each glow loop being a loop of resistance wire;

a radio frequency (RF) generator; and one or two loop power supplies respectively corresponding to the one or two glow loops, each loop power supply configured to independently supply sufficient electrical current to its respective glow loop to heat the resistance wire of its respective glow loop to a glow, wherein the RF generator and the one or two loop power supplies are configured to operate concurrently, while the one or two glow loops are heated to said glow, to supply both sufficient RF power and associated electrical current across the living tissue for cutting and/or coagulating the living tissue by the one or two glow loops, and wherein a first output of the RF generator is electrically coupled to the one or two glow loops.

The present invention provides a method, comprising cutting and/or coagulating living tissue with one or two heated loops of resistance wire accompanied by sufficient electrical current across the living tissue to enable said cutting and/or coagulating to be performed The present invention overcomes at least one of the disadvantages (identified supra) of conventional electrosurgical devices.

DETAILED DESCRIPTION OF THE INVENTION

The invention discloses a substantial improvement over the conventional electrosurgical device. The improvement allows for equivalent cutting with coagulation using reduced power and voltage, hence less current, yielding more precise cutting, less tissue trauma, faster healing and improved safety for patient and surgeon. With the conventional electrosurgical unit the high voltage is necessary to initiate and maintain a current path from the cutting probe to target tissue. This is a form of ionization at room temperatures and pressure. To accomplish this continuous arc, high voltage is essential.

The key feature of the improvement is use of a GLOWING cutting probe that is "ready and able" to give off electrons to initiate and maintain an arc to the target tissue. The glowing probe is called a Glow Blade™ and consists of a loop of resistance wire heated to a cherry red color by electrical current. This is similar to a filament in a vacuum tube which is also heated to promote electron emission from "filament to plate" or "cathode to plate" elements of the vacuum tube. The Glow Blade is electrically connected to the RF generator hot lead. It is the RF excited and glowing filament of wire that is cutting the tissue. The cutting energy is primarily supplied by the RF generator. As the tissue is cut, coagulation as a result of RF heating immediately stops bleeding.

An alternative mode of operation totally eliminates the patient ground pad and associated currents which would otherwise travel through the patient's body. This is accomplished by using a Dual Glow Blade. Here two heated filaments in the form of a loop are placed, side by side, nearly touching. In this scenario, the RF generator is connected across the two glowing loops.

When the glowing filaments touch the patient's tissue, current flows from one loop to the other via the tissue, affecting a cut. If this approach were attempted with a conventional electrosurgical technology using unheated loops, the required higher voltage would arc and short one loop to the other due to carbon and tissue debris between the loops. With the Dual Glow Blade and lower voltage plus constant glowing of cutting loops to burn away debris, arcing is eliminated. Tissue cutting with this Dual Glow Blade is practical and eliminates the patient pad and undesirable body currents. As with a single loop, cutting is achieved along with coagulation, thus eliminating loss of blood.

The present invention provides an electrosurgical apparatus having a glow blade for cutting and/or coagulating living tissue of a mammal. The phrase "cutting and/or coagulating" means cutting, coagulating, or both cutting and coagulating. Although specific embodiments of the present invention are described infra with respect to cutting and/or coagulating living tissue of a person or patient, the electrosurgical apparatus of the present invention may be employed generally for cutting and/or coagulating living tissue of a mammal. The mammal may be a human being such as, inter alia, a person in an operating room of a hospital or in a doctor's office, a soldier wounded in combat, etc. Alternatively, the mammal may be a non-human mammal (e.g., a rat, a dog, etc.).

The electrosurgical apparatus of the present invention provides advantages which include:

(1) a lower power electrosurgical unit for coagulating tissue as it cuts;
(2) reduced power cutting (up to 5 times lower than with conventional electrosurgical units);
(3) more precise and smooth cutting;
(4) less smoke form cutting;
(5) a cleaner cut;
(6) less patient trauma;
(7) faster healing;
(8) no carbon buildup on cutting blade;
(9) no carbon buildup on patient tissue;
(10) improved safety for patent and surgeon with lower voltage and power;
(11) even cutting at depth of blade;
(12) elimination of patient pad for dual glow blade approach;
(13) no sticking of cutting blade to tissue; and
(14) rapid coagulation of tissue which stops uncontrolled bleeding of soldiers wounded in combat.

Thus, the electrosurgical apparatus of the present invention discloses a substantial improvement over the conventional electrosurgical device. The improvement allows for cutting of tissue with accompanying coagulation, using reduced power and voltage, hence less current, yielding more precise cutting, less tissue trauma, faster healing, and improved safety for patient and surgeon. Moreover, the electrosurgical apparatus of the present invention may be used for rapid coagulation of tissue (with or without accompanying cutting) in order to stop bleeding immediately (e.g.; to stop uncontrolled bleeding of soldiers wounded in combat). This rapid coagulation has not been previously practical in a battery powered field unit. With the present invention, however, a battery-powered unit is now practical.

The present invention provides an electrosurgical apparatus for cutting and coagulating living tissue. The electrosurgical apparatus comprises a glow blade, a radio frequency (RF) generator, and one or two loop power supplies. The glow blade has one or two glow loops, each glow loop being a loop of resistance wire. The RF generator supplies RF energy for cutting and coagulating living tissue by the glow blade. The one or two loop power supplies respectively correspond to the one or two glow loops, each loop power supply adapted to independently supply sufficient electrical current to its respective glow loop to heat the resistance wire of its respective glow loop to a glow to enable the one or two glow loops to cut and coagulate the living tissue. The RF generator and the one or two loop power supplies are configured to operate concurrently, while the one or two glow loops are heated to a glow, to supply both sufficient RF power and associated electrical current across the living tissue for cutting and coagulating the living tissue by the one or two glow loops. A first output of the RF generator is electrically coupled to the one or two glow loops.

A first loop power supply of the one or two loop power supplies is configured such that there is no electrical current path from any output of the RF generator into the first loop power supply.

The present invention provides an electrosurgical apparatus for coagulating living tissue. The electrosurgical apparatus comprises a glow blade, a radio frequency (RF) generator, and one or two loop power supplies. The glow blade has one or two glow loops, each glow loop being a loop of resistance wire. The RF generator supplies RF energy for coagulating living tissue by the glow blade. The one or two loop power supplies respectively correspond to the one or two glow loops, each loop power supply adapted to independently supply sufficient electrical current to its respective glow loop to heat the resistance wire of its respective glow loop to a glow such that the glow loop is ready and able to give off electrons to enable the one or two glow loops to coagulate the living tissue. The RF generator and the one or two loop power supplies are configured to operate concurrently, while the one or two glow loops are heated to a glow, to supply both sufficient RF power and associated electrical current across the living tissue for coagulating the living tissue by the one or two glow loops. A first output of the RF generator is electrically coupled to the one or two glow loops.

A first loop power supply of the one or two loop power supplies is configured such that there is no electrical current path from any output of the RF generator into the first loop power supply.

In alternative glow blade embodiments, the glow blade may be a single glow blade or a dual glow blade.

Single Glow Blade Embodiment

Figure 1:
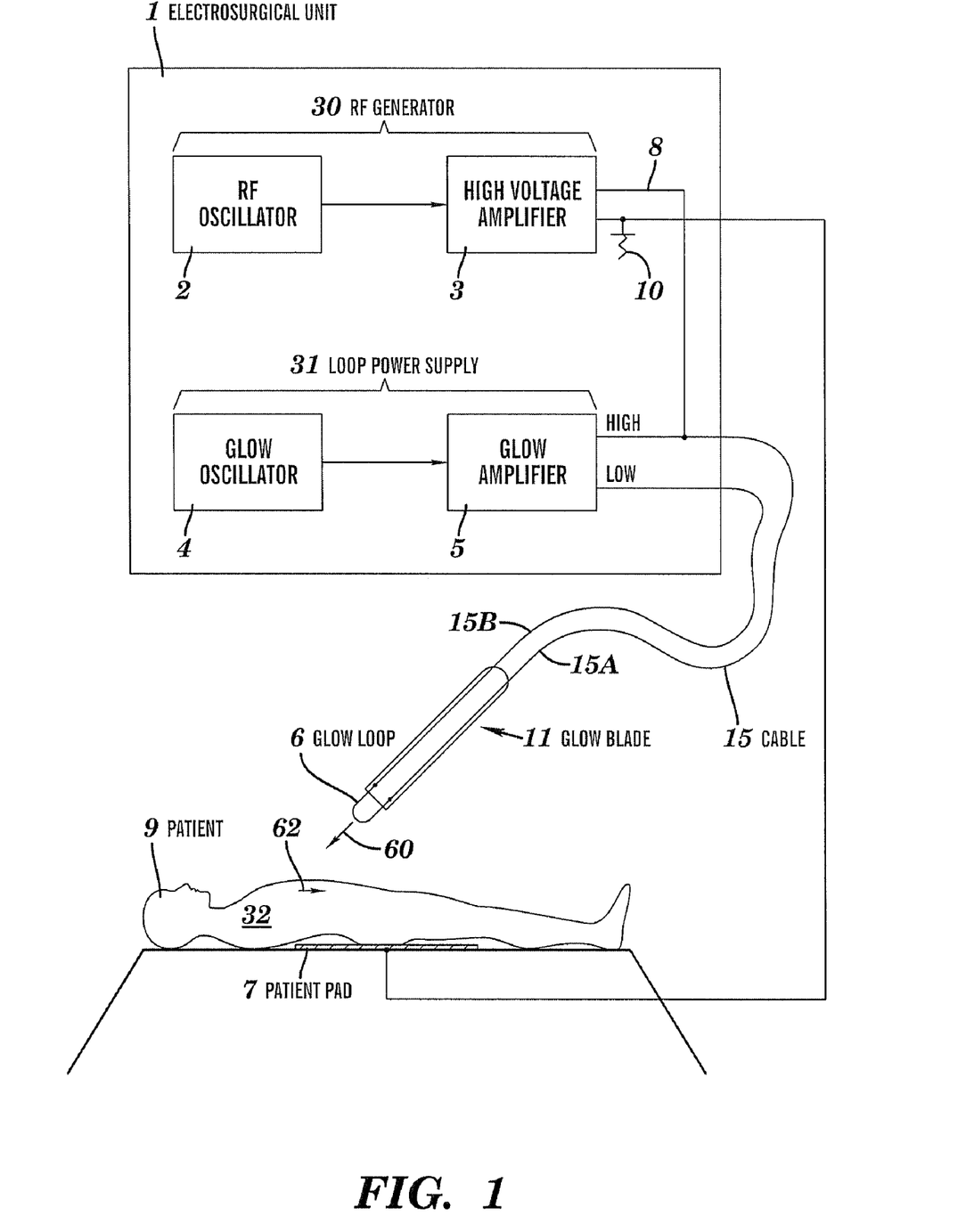
FIG. 1 depicts an electrosurgical apparatus in a single ended mode with a single glow blade for use with a patient, in accordance with embodiments of the present invention.

FIG. 1 depicts an electrosurgical apparatus in a single ended mode with a single glow blade for use with a patient, in accordance with embodiments of the present invention. The electrosurgical unit apparatus of FIG. 1 may be powered by alternating current (AC) power, direct current (DC) power such via batteries (e.g., isolated rechargeable batteries), or by a combination of AC power and DC power.

Figure 8:
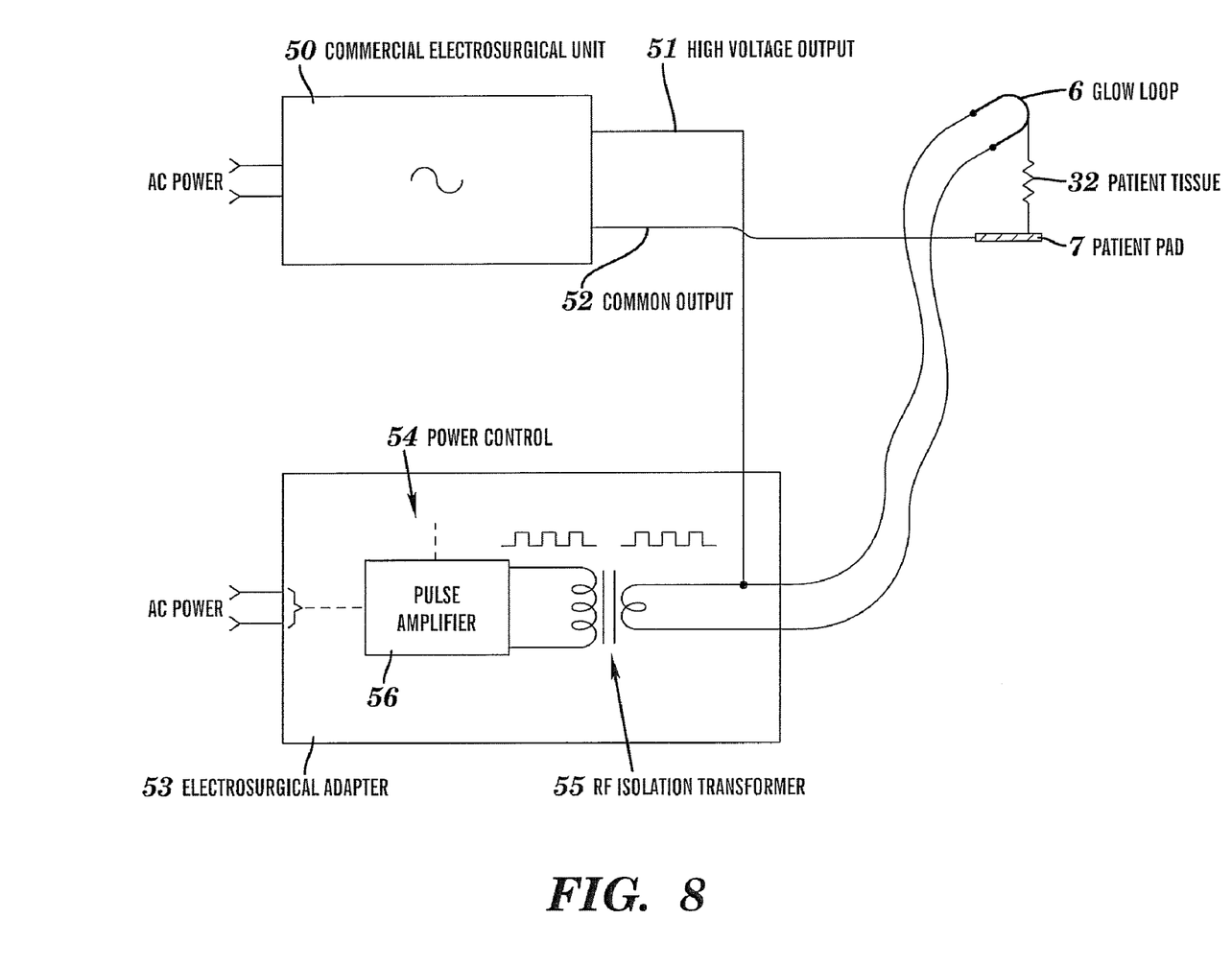
FIG. 8 depicts an alternative electrosurgical apparatus in a single ended mode with a single glow blade for use with a patient, in accordance with embodiments of the present invention.

The electrosurgical apparatus of FIG. 1 comprises an electrosurgical unit 1 and a glow blade 11, which may be contained within a single enclosure as shown in FIG. 1 or may be provided in separate enclosures as depicted in FIG. 8 described infra. The electrosurgical unit 1, which comprises a radio frequency (RF) generator 30 and a loop power supply 31, is electrically connected to the glow blade 11 by cable 15 which comprises conductors 15A and 15B. The loop power supply 31 is configured such that there is no electrical current path from any output of the RF generator into the loop power supply 31.

The glow blade 11 comprises a glow loop 6 which functions as a cutting probe that maintains an arc, wherein the arc cuts the target tissue. The glow loop 6 is a loop of resistance wire heated to a glow (e.g., a cherry red color) by electrical current. The glowing of the glow loop 6 may be analogous to a filament in a vacuum tube that is heated to promote electron emission from "filament to plate" or "cathode to plate" elements of the vacuum tube. Thus, it should be understood that the glow loop 6 is ready and able to give off electrons.

The glow loop 6 is electrically connected to the hot lead 8 of the RF generator 30. The glow loop 6 is RF excited such that the glowing filament of the resistance wire of the glow loop 6 cuts tissue 32 of a patient 9. Thus, the tissue 32 is living tissue. The RF generator 30 supplies the cutting energy and also causes RF heating of the tissue 32. As the tissue 32 is cut, coagulation of tissue results from the RF heating, which immediately stops bleeding.

Figure 7:
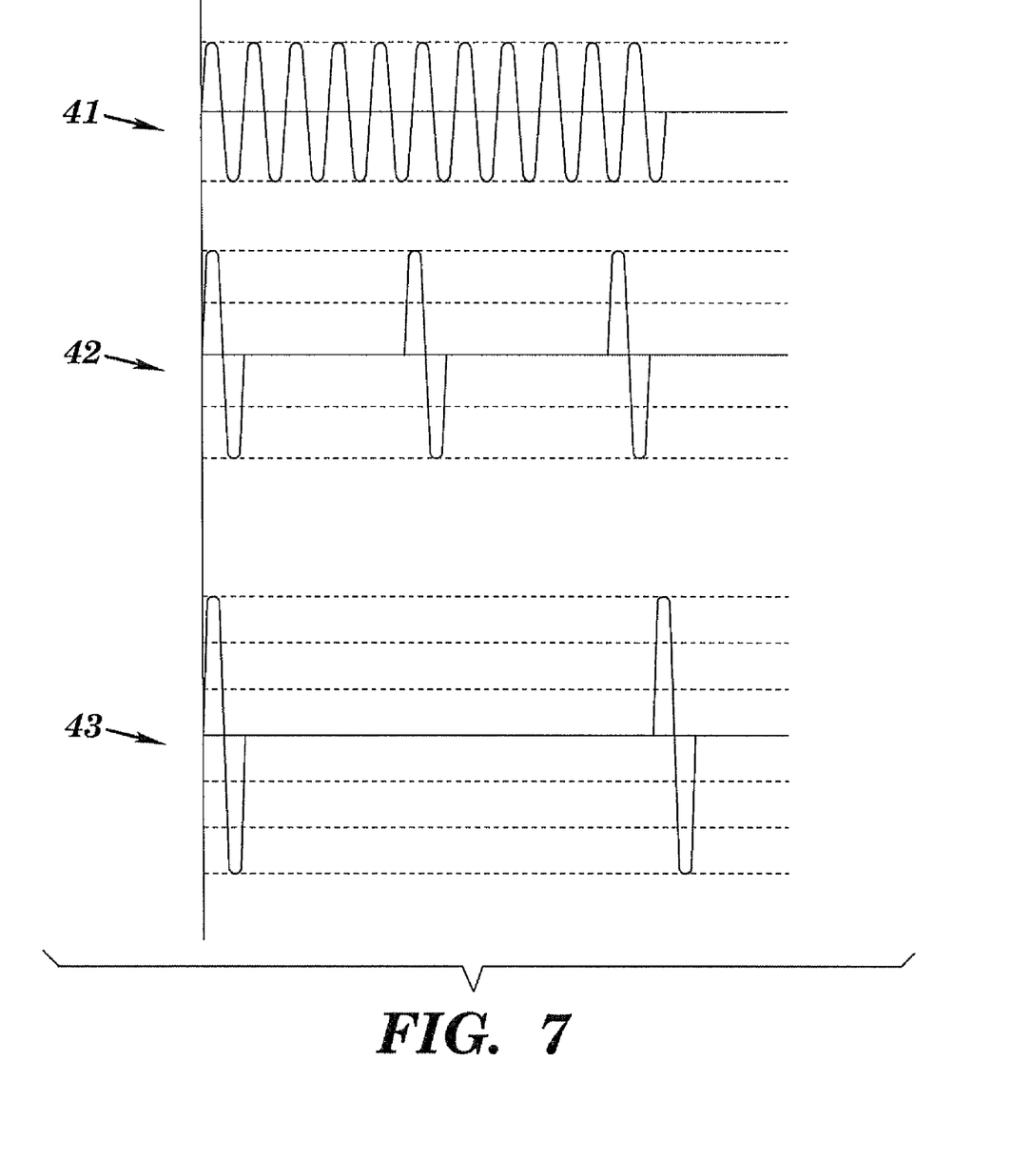
FIG. 7 depicts examples of radio frequency (RF) generator output wave shapes, in accordance with embodiments of the present invention.

The RF generator 30, which supplies RF energy for tissue cutting, comprises a RF oscillator 2 and a high voltage (HV) amplifier 3, wherein the RF oscillator 2 drives the high voltage amplifier 3. The RF oscillator 2 has an operating frequency between 100 KHz and 10 MHz (e.g., 500 KHz). The high voltage amplifier 3 generates variable wave shapes, including modulated types. For example, FIG. 7 depicts examples of radio frequency (RF) generator output wave shapes, in accordance with embodiments of the present invention. In FIG. 7, a continuous wave (i.e., 100% duty cycle) is shown in wave shape 41 with amplitude of 100 volts RMS. A modulated shape of approximately 30% duty cycle is shown at wave shape 42 with higher amplitude than wave shape 41. The duty cycle of the modulated shape is defined as the ratio of the pulse duration in each cycle to the cycle period. A modulated shape of approximately 10% duty cycle is shown at wave shape 43, with much higher amplitude than wave shape 41. Different wave shapes may be employed for different procedures (e.g., cutting with accompanying coagulation; coagulation without accompanying cutting; etc; etc.). For example, modulated pulse shapes having duty cycles from about 20% to about 100%, which include the wave shapes 41 and 42 of FIG. 7, may be employed for cutting with accompanying coagulation. As another example, modulated pulse shapes having duty cycles from about 2% to about 20%, which include the wave shape 43 of FIG. 7, may be employed for coagulation without accompanying cutting. Moreover, wave shape 41 may be alternatively employed for pure cutting without accompanying coagulation.

The variable wave shapes have an associated time-averaged output that may be varied from 50 to 500 volts (e.g., a sine wave with 100 volts RMS output voltage). Successful tissue cutting will occur, inter alia, with 100 volts while consuming only 5 watts of power, which implies a power range of 1.25 to 125 watts for the output voltage range of 50 to 500 volts. The lower output voltage of the RF generator 30, as compared the much higher output voltage of at least 1000 volts of a conventional electrosurgical device, results in lower current through the target tissue and bulk of the patient 9.

The loop power supply 31 comprises a glow oscillator 4 and glow amplifier 5, wherein the glow oscillator 4 drives the glow amplifier 5. The output of the glow amplifier 5 is a low-voltage, high-current signal to "light up" the glow loop 6 of the glow blade 11. By adjusting the duty cycle of the glow oscillator 4, one can adjust the brightness or temperature of glow loop 6. The glow elements (i.e., the glow oscillator 4 and the glow amplifier 5) are like a variable battery connected across a light bulb. The glow oscillator 4 and glow amplifier 5 could be replaced by any suitable adjustable power source. In one embodiment, the loop power supply 31 is a DC source (e.g., one or more batteries) that drives a pulse amplifier to generate a pulse train that is sent to the glow loop 6. The power of the pulse train from the loop power supply 31 controls the temperature of the glow loop 6, which controls the brightness of the glow loop 6. The power of the pulse train from the loop power supply 31 may be varied by adjustment of the pulse amplitude, duty cycle and/or the pulse frequency. In one embodiment, the power source for the loop power supply 31 is an AC power source such as 115 VAC mains (e.g., the electrosurgical adapter 53 of FIG. 8, described infra).

The RF generator 30 is electrically coupled to the loop power supply 31. The hot lead 8 of the high voltage amplifier 3 is electrically connected to both the output high side of the glow amplifier 5 and a first portion of the glow loop 6 via conductor 15A. The output low side of glow amplifier 5 is electrically connected to a remaining portion of the glow loop 6 via conductor 15B. Those skilled in the art realize that the outputs of supply 31 are reversible; i.e., high can be swapped with low and vice versa. The circuit ground 10 of the high voltage amplifier 3 is electrically connected to patient pad 7 which is in physical and electrical contact with the patient 9 such as, inter alia, the patient 9 lying on the pad 7. The hot lead 8 output (via circuit ground 10) of the RF generator 30 is electrically connected to the pad 7 to facilitate an electric current flowing through the tissue of the patient 9 between the glow loop 6 and the pad 7. The circuit ground 10 is actually a return path for the hot lead 8 output and is sometimes called ground or minus terminal, where such ground is sometimes used as a convenience designation and does not necessarily imply any connection to earth ground. For example the RF generator 30 may incorporate an output transformer where it is common practice to float output common from earth ground for safety reasons.

When the glow loop 6 touches the patient 9, RF current flows from glow loop 6 through the target tissue, through the bulk of the patient 9, and to the patient pad 7. The cutting of the tissue 32 occurs at the points of contact between the glow loop 6 and the patient 9. As the glow loop 6 is moved into the tissue, in a direction 60 parallel to the axis of glow loop 6, tissue of the patient 9 is cut.

Figures 5, 6A, 6B:
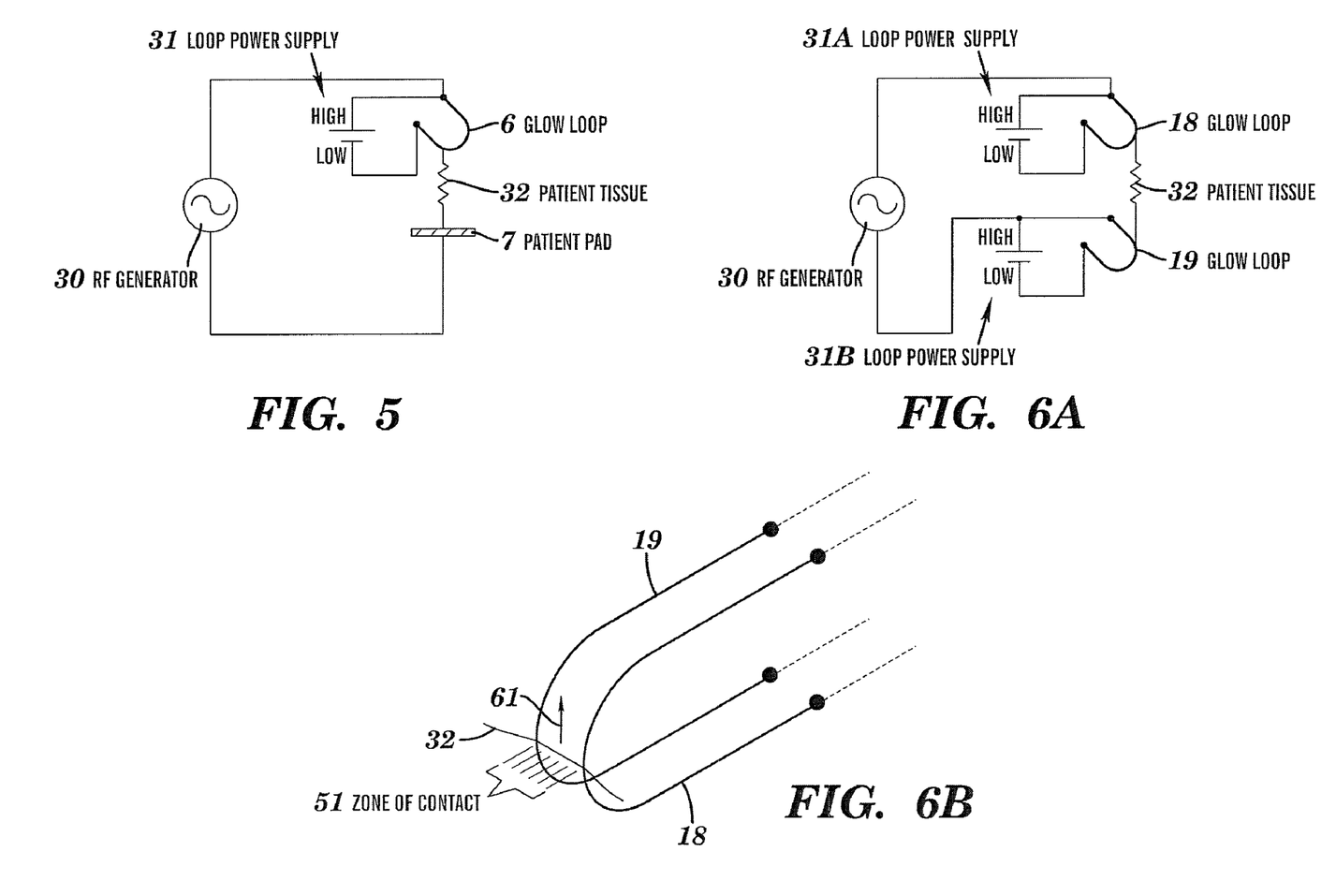
FIG. 5 depicts an equivalent electric circuit representing the electrosurgical apparatus and patient of FIG. 1, in accordance with embodiments of the present invention.
FIG. 6A depicts an equivalent electric circuit representing the electrosurgical apparatus and patient of FIG. 2, in accordance with embodiments of the present invention.
FIG. 6B is an isometric view of glow loops in FIG. 6A, in accordance with embodiments of the present invention.

FIG. 5 depicts an equivalent electric circuit representing the electrosurgical apparatus and patient of FIG. 1, in accordance with embodiments of the present invention. In FIG. 5, the RF generator 30 connects to the high side of glow loop 6. The loop power supply 31 is shown simplistically as a battery and connects across the glow loop 6. The glow loop 6 is shown in electrical contact with patient tissue 32, indicated as a resistive element. A portion of this resistive element adjacent to the patient pad 7 is the remainder of the patient which touches the patient pad 7. The patient pad 7 is electrically connected back to the RF generator 30 common at circuit ground 10. The battery lights up the glow loop 6 and RF power is connected to the glow loop 6 which in turn transports energy to cut the tissue 32 of the patient 9. The RF current path is from the RF generator 30 to the glow loop 6, through the tissue being cut, through the bulk of the patient, to the pad 7 and back to the RF generator 30. The battery current path is through the glow loop 6 to heat the glow loop 6, so as to facilitate the transport of RF energy to the target tissue 32. The RF current through the patient tissue 32 achieves the cutting of the tissue 32 of the patient 9. Because the applied RF voltage is substantially lower than the voltage of the conventional electrosurgical devices, lower and safer current flows through the patient as a result of usage of the single glow blade electrosurgical apparatus of the current invention.

Figure 3:
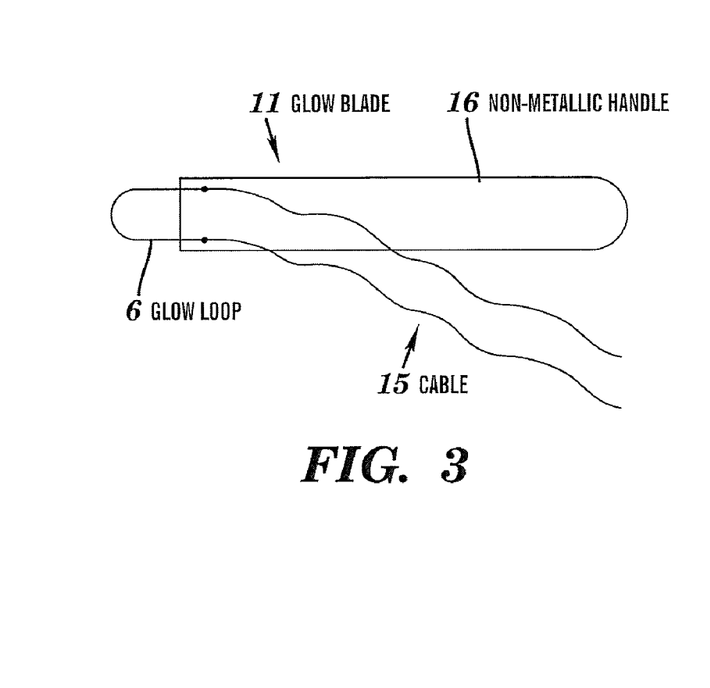
FIG. 3 depicts the single glow blade of FIG. 1 in greater detail, in accordance with embodiments of the present invention.

FIG. 3 depicts the single glow blade 11 of FIG. 1 in greater detail, in accordance with embodiments of the present invention. Cable 15 simultaneously provides both RF and glow power to glow loop 6 from RF generator 30 and glow amplifier 5, respectively. A non-metallic handle 16 supports the glow loop 6. The glow loop 6 may be constructed with resistance wire such as nickel, chrome, stainless steel, or other suitable material. The size and shape of the glow loop 6 will vary depending on type of surgical procedure. In one embodiment, the approximate size of the glow loop 6 is that of a conventional surgical knife such as a #11 blade or a #10 skin blade. The cross section of the glow loop 6 may be round, rectangular, or flat, with typical cross section diameter of the glow loop 6 ranging from 0.001 to 0.10 inches (e.g., 0.005 inches). The glow loop 6 may be circular, or long and slender. If the glow loop 6 is long and slender, then the slender portion could have curvature for excising tissue of a curved shape.

FIG. 8 depicts an alternative electrosurgical apparatus in a single ended mode with a single glow blade for use with the patient 9 of FIG. 1, in accordance with embodiments of the present invention. The electrosurgical apparatus of FIG. 8 differs from the electrosurgical apparatus of FIGS. 1 and 5 in that: a commercial electrosurgical unit 50 of FIG. 8 replaces the RF generator 30 of FIGS. 1 and 5; and the electrosurgical adapter 53 of FIG. 8 replaces the loop power supply 31 of FIGS. 1 and 5. In all other respects, the electrosurgical apparatus of FIG. 8 and the electrosurgical apparatus of FIGS. 1 and 5 are essentially the same electrosurgical apparatus with respect to structure and functionality.

The commercial electrosurgical unit 50 is the RF power portion of a conventional electrosurgical apparatus used in the prior art. The glow blade 11 (see FIG. 1) comprises the glow loop 6 and operates in conjunction with the electrosurgical adapter 53. The commercial electrosurgical unit 50 receives AC power as shown and has a high voltage output 51 and a common output 52 connected to circuit ground. The high voltage output 51 is electrically connected, via the electrosurgical adapter 53, to glow loop 6 which contacts the patient tissue 32. The common output 52 is electrically tied to the patient pad 7. The electrosurgical adapter 53, which converts AC power to a pulse train to provide power to the glow loop 6, comprises a pulse generator/amplifier 56 and a RF isolation transformer 55. An operator power control 54 connects to the pulse generator/amplifier 56 and controls the power in the pulse train by varying pulse rate, duty cycle, or amplitude of the pulse train, which controls the temperature of the glow loop 6. The RF isolation transformer 55 allows power to be coupled from the pulse amplifier 56 to the glow loop 6 while providing a high impedance for any stray RF current flowing from the electrosurgical unit 50. The transformer 55 is wound with sufficient distance between primary and secondary coils to achieve the required power to be supplied to the glow loop 6. In one embodiment, the electrosurgical adapter 53 may be replaced by a battery such as a battery representing the loop power supply 31 of FIGS. 1 and 5, for use with the commercial electrosurgical unit 50.

The output from the electrosurgical adapter 53 of FIG. 8 is analogous to the output from the loop power supply 31 of FIG. 1. In FIG. 1, the output of the loop power supply 31 is electrically decoupled from the AC power source of the RF generator 30 (e.g., by use of a battery as a power source of the loop power supply 31), which prevents unwanted RF power from flowing from the RF generator 30 to the power source of the loop power supply 31. Similarly in FIG. 8, the output of the electrosurgical adapter 53 is electrically decoupled from its AC power source and hence the power source of the electrosurgical unit 50 due to the output of the electrosurgical adapter 53 being decoupled by the RF isolation transformer 55, which prevents unwanted RF power from flowing from the electrosurgical adapter 53 to the power source of the electrosurgical adapter 53.

The single glow blade may be used for rapid coagulation of tissue (without accompanying cutting of tissue) in order to stop bleeding immediately (e.g.; to stops uncontrolled bleeding of soldiers wounded in combat). In one embodiment for such coagulation applications, the glow loop 6 may be may be brushed along the surface of the tissue being coagulated (e.g., moved in a brushing-type motion in a direction that is about parallel to the surface of the tissue being coagulated; e.g., about in the direction 62 in FIG. 1). Successful coagulation of tissue (without accompanying cutting of tissue) will occur with output power from the RF generator in a range of 1.25 to 125 watts.

Thus the RF generator 30 and the loop power supply 31 are configured to operate concurrently, while the glow loop 6 is heated to a glow, to supply both sufficient RF power and associated electrical current across the living tissue 32 for cutting and/or coagulating the living tissue 32 by the glow loop 6.

The inventor of the present invention has determined that the single glow blade embodiment of the present invention may be beneficially employed in a non-glowing mode for the glow loop, as an improvement over conventional electrosurgical devices of the prior art, if the single glow blade embodiment is implemented as described supra except that the glow loop 6 performs cutting and/or coagulation of tissue at a temperature below the minimum glow temperature of the material of the glow loop 6 (e.g., at a temperature in a range of about 300° F. to just below the minimum glow temperature). The minimum glow temperature of the material is defined as the minimum temperature at which the material glows (i.e., emits electromagnetic radiation in the visible portion of the electromagnetic spectrum).

Dual Glow Blade Embodiment

The dual glow blade embodiment provides an alternative mode of operation that totally eliminates the patient pad of the single glow blade and eliminates associated currents which would otherwise travel through the patient's body. Two heated filaments, each in the form of a loop, are placed, side by side, nearly touching each other and made to glow. In this scenario, the RF generator is connected across the two glowing loops. When the glowing filaments touch the patient's tissue, current flows from one loop to the other loop via the tissue that contacts the perimeter of the loops. If this approach were attempted with a conventional electrosurgical technology using unheated loops, the required higher voltage would arc and short one loop to the other due to carbon and tissue debris between the loops. With the dual glow blade and lower voltage plus constant glowing of cutting loops to burn away debris, arcing is eliminated. Tissue cutting with this dual glow blade is practical and eliminates the patient pad and undesirable body currents. As with a single loop, cutting is achieved along with coagulation of tissue, wherein the coagulation reduces or eliminates loss of blood.

Figure 2:
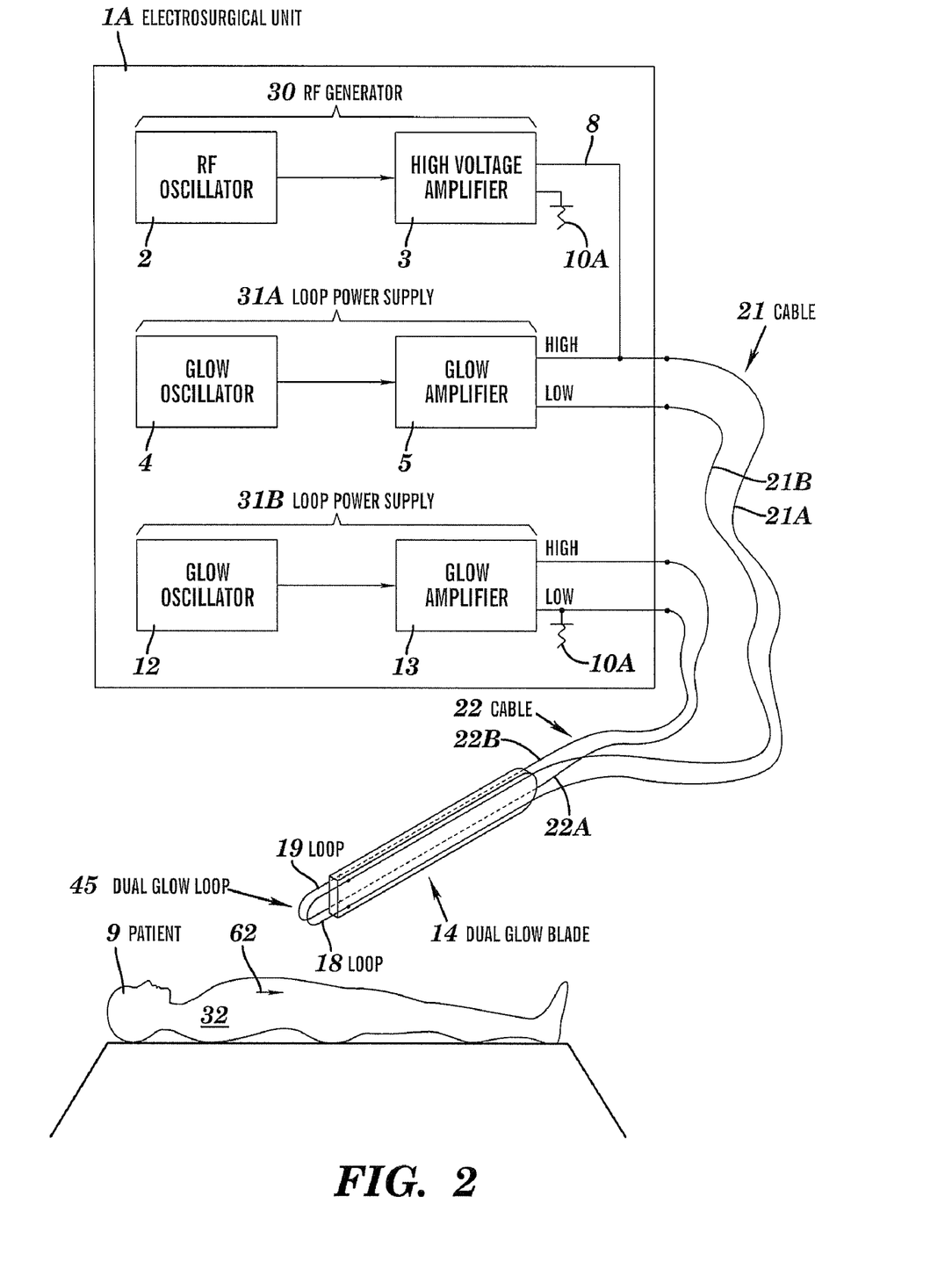
FIG. 2 depicts an electrosurgical apparatus configured for differential operation with a dual glow blade for use with a patient, in accordance with embodiments of the present invention.

FIG. 2 depicts an electrosurgical apparatus configured for differential operation with a dual glow blade for use with a patient, in accordance with embodiments of the present invention. The electrosurgical unit apparatus of FIG. 2 may be powered by alternating current (AC) power, direct current (DC) power such via batteries (e.g., isolated rechargeable batteries), or by a combination of AC power and DC power.

Figure 9:
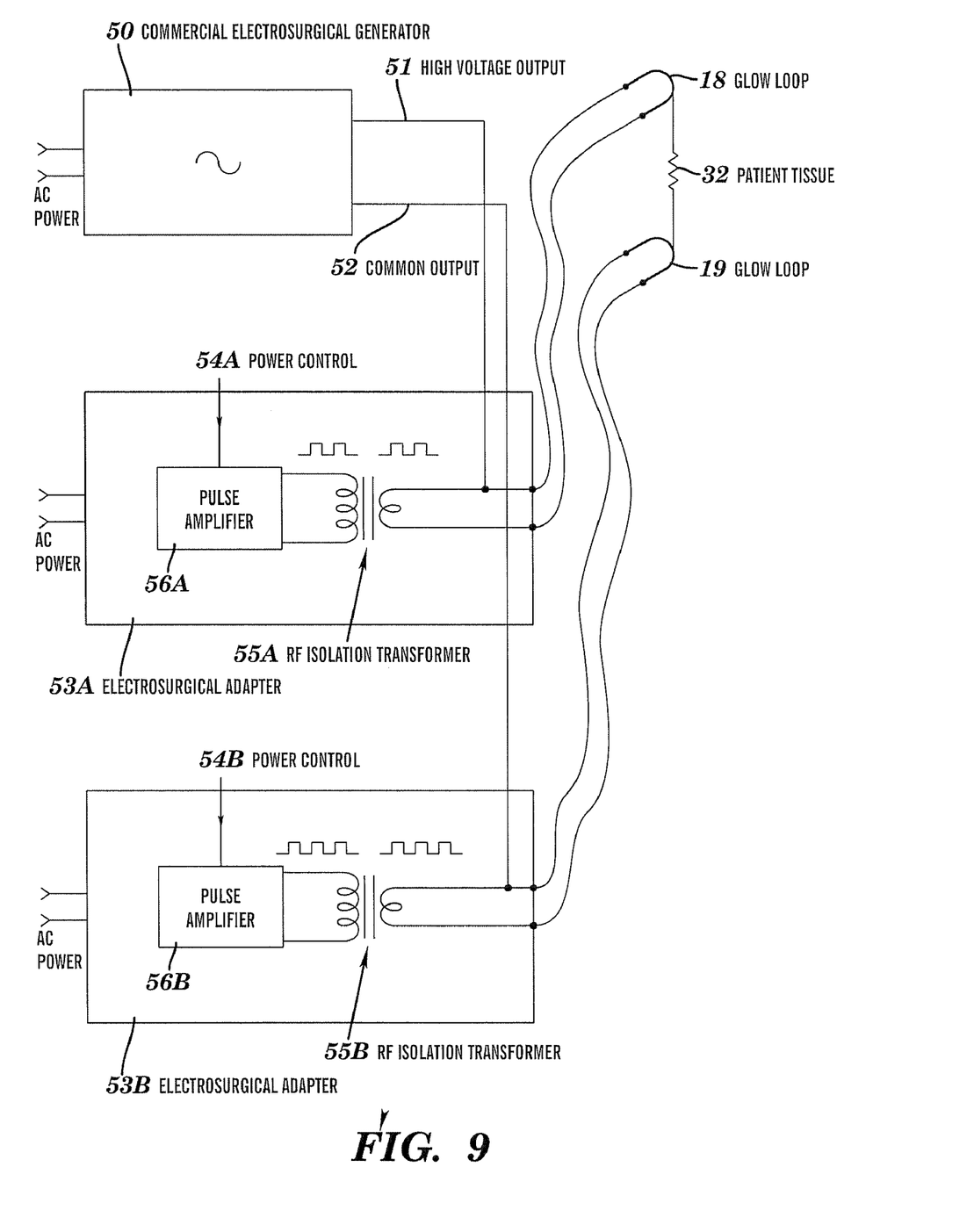
FIG. 9 depicts an alternative electrosurgical apparatus configured for differential operation with a dual glow blade for use with a patient, in accordance with embodiments of the present invention.

The electrosurgical apparatus of FIG. 2 comprises an electrosurgical unit 1A and a dual glow blade 14, which may combined in a single enclosure as shown in FIG. 2 or may be provided in separate enclosures as depicted in FIG. 9 described infra. The electrosurgical unit 1A, which comprises a radio frequency (RF) generator 30, a loop power supply 31A, and a loop power supply 31B, is electrically connected to the dual glow blade 14 by cable 21 and cable 22, respectively. The loop power supply 31A is analogous to the loop power supply 31 of FIG. 1 and the loop power supply 31B is an added loop power supply which may be similar to, or identical with, the loop power supply 31A. Cable 21 comprises conductors 21A and 21B. Cable 22 comprises conductors 22A and 22B.

The loop power supply 31A is configured such that there is no electrical current path from any output of the RF generator into the loop power supply 31A.

The dual glow blade 14 comprises glow dual glow loop 45 which functions as a cutting probe that maintains an arc, wherein the arc cuts the target tissue. The glow dual glow loop 45 comprises glow loops 18 and 19. As with the glow loop 16 of FIG. 1, the glow loops 18 and 19 are loops of resistance wire heated to a glow (e.g., a cherry red color) by electrical current. As compared to FIG. 1, the patient pad 7 has been eliminated in FIG. 2, and the RF cutting voltage appears across the glow loops from glow loop 18 to glow loop 19. When the loops of dual glow blade 14 comes in contact with the patient tissue 32 (which is living tissue), cutting is achieved. As the tissue 32 is cut, coagulation of tissue results from the RF heating, which immediately stops bleeding.

The RF generator 30, which supplies RF energy for tissue cutting, comprises a RF oscillator 2 and a high voltage (HV) amplifier 3, wherein the RF oscillator 2 drives the high voltage amplifier 3. The RF oscillator 2 has an operating frequency between 100 KHz and 10 MHz (e.g., 500 KHz). The high voltage amplifier 3 generates variable wave shapes, including modulated types. The high voltage amplifier 3 generates variable wave shapes, including modulated types. For example, FIG. 7 depicts examples of radio frequency (RF) generator output wave shapes, in accordance with embodiments of the present invention. In FIG. 7, a continuous wave (i.e., 100% duty cycle) is shown in wave shape 41 with amplitude of 100 volts RMS. A modulated shape of approximately 30% duty cycle is shown at wave shape 42 with higher amplitude than wave shape 41. The duty cycle of the modulated shape is defined as the ratio of the pulse duration in each cycle to the cycle period. A modulated shape of approximately 10% duty cycle is shown at wave shape 43, with much higher amplitude than wave shape 41. Different wave shapes may be employed for different procedures (e.g., cutting with accompanying coagulation; coagulation without accompanying cutting; etc; etc.). For example, modulated pulse shapes having duty cycles from about 20% to about 100%, which include the wave shapes 41 and 42 of FIG. 7, may be employed for cutting with accompanying coagulation. As another example, modulated pulse shapes having duty cycles from about 2% to about 20%, which include the wave shape 43 of FIG. 7, may be employed for coagulation without accompanying cutting. Moreover, wave shape 41 may be alternatively employed for pure cutting without accompanying coagulation.

The variable wave shapes have an associated time-averaged output that may be varied from 50 to 500 volts (e.g., a sine wave with 100 volts RMS output voltage). Successful tissue cutting will occur, inter alia, with 100 volts while consuming only 5 watts of power, which implies a power range of 1.25 to 125 watts for the output voltage range of 50 to 500 volts. The lower output voltage of the RF generator 30, as compared the much higher output voltage of at least 1000 volts of a conventional electrosurgical device, results in lower current through the target tissue and bulk of the patient 9.

The loop power supply 31A comprises the glow oscillator 4 and glow amplifier 5, wherein the glow oscillator 4 drives the glow amplifier 5. The output of the glow amplifier 5 is a low-voltage, high-current signal to "light up" the glow blade loop 18 of the glow blade 14. By adjusting the duty cycle of the glow oscillator 4, one can adjust the brightness or temperature of glow loop 18. The glow elements (i.e., the glow oscillator 4 and the glow amplifier 5) are like a variable battery connected across a light bulb. The glow oscillator 4 and glow amplifier 5 could be replaced by any suitable adjustable power source. In one embodiment, the loop power supply 31A is powered by a DC source (e.g., one or more batteries) that drives a pulse amplifier to generate a pulse train that is sent to the glow loop 18. The power of the pulse train from the loop power supply 31A controls the temperature of the glow loop 18, which controls the brightness of the glow loop 18. The power of the pulse train from the loop power supply 31A may be varied by adjustment of the pulse amplitude, duty cycle and/or the pulse rate. In one embodiment, the power source for the loop power supply 31A is an AC power source such as 115 VAC mains (e.g., the electrosurgical adapter 53A of FIG. 9, described infra).

The loop voltage loop power supply 31B comprises the glow oscillator 12 and glow amplifier 13, wherein the glow oscillator 12 drives the glow amplifier 13. The output of the glow amplifier 13 is a low-voltage, high-current signal to "light up" the glow loop 19 of the glow blade 14. By adjusting the duty cycle of the glow oscillator 4, one can adjust the brightness or temperature of glow loop 19. The glow elements (i.e., the glow oscillator 12 and the glow amplifier 13) are like a variable battery connected across a light bulb. The glow oscillator 12 and glow amplifier 13 could be replaced by any suitable adjustable power source. In one embodiment, the loop power supply 31B is a DC source (e.g., one or more batteries) that drives a pulse amplifier to generate a pulse train that is sent to the glow loop 19. The power of the pulse train from the loop power supply 31B controls the temperature of the glow loop 19, which controls the brightness of the glow loop 19. The power of the pulse train from the loop power supply 31B may be varied by adjustment of the pulse amplitude, duty cycle and/or the pulse rate. In one embodiment, the power source for the loop power supply 31B is an AC power source such as 115 VAC mains (e.g., the electrosurgical adapter 53B of FIG. 9, described infra).

The RF generator 30 is electrically coupled to the power supplies 31A and 31B. The hot lead 8 of the high voltage amplifier 3 is electrically connected to the high side of the glow amplifier 5 as in FIG. 1 and also to the glow loop 18. The low side of the high voltage amplifier 3 is electrically connected in FIG. 2 to an internal circuit ground 10A which is also electrically connected to the low side of the glow amplifier 13 and to loop 19. Outputs of the glow amplifier 5 and the glow amplifier 13 are electrically connected to and across the glow loops 18 and 19 of the dual glow blade 14 via cable 21 and 22, respectively. When the glow loops 18 and 19 touch the patient 9, the tissue 32 of the patient 9 is cut by the extremities of the glow loops.

FIG. 6A depicts an equivalent electric circuit representing the electrosurgical apparatus and patient of FIG. 2, in accordance with embodiments of the present invention. In FIG. 6A the high side of the RF generator 30 is electrically connected to the high side of the glow loop 18. The low side or common of the RF generator 30 is electrically connected to the high side of the glow loop 19. The power supplies 31A and 31B are represented simplistically as batteries and connect across the glow loops 18 and 19 but may alternatively be represented by AC power sources. The power supplies 31A and 31B light up the glow loops 18 and 19, respectively, while the RF generator 30 provides energy for tissue cutting. The glow loops 18 and 19 are physically planar on a common axis and are thus parallel to each other, with a gap between the glow loops 18 and 19. Those skilled in the art realize that the outputs of each respective supply 31A and 31B are reversible; i.e.; high can be swapped with low and vice versa.

FIG. 6B is an isometric view of the glow loops 18 and 19 of FIG. 6A, in accordance with embodiments of the present invention. FIG. 6B shows the parallel planar glow loops 18 and 19 with their edges in contact with tissue 32 in a zone of contact 51. The cutting of the tissue 32 occurs in this zone of contact 51, because the RF current passes from glow loop 18 through the target tissue 32 to glow loop 19, due to the voltage across the gap between the glow loops 18 and 19. Cutting of the tissue 32 is accomplished as the glow loops 18 and 19 are moved into and across the tissue 32 in a direction 61 parallel to the plane of glow loop 18 and the plane of glow loop 19. Because the applied RF voltage is substantially lower than the voltage of the conventional electrosurgical devices, lower and safer current flows through the tissue 32 at the zone of contact 51 between glow loops 18 and 19, without arcing and carbonization of tissue, as a result of usage of the dual glow blade electrosurgical apparatus of the current invention.

Figure 4A:
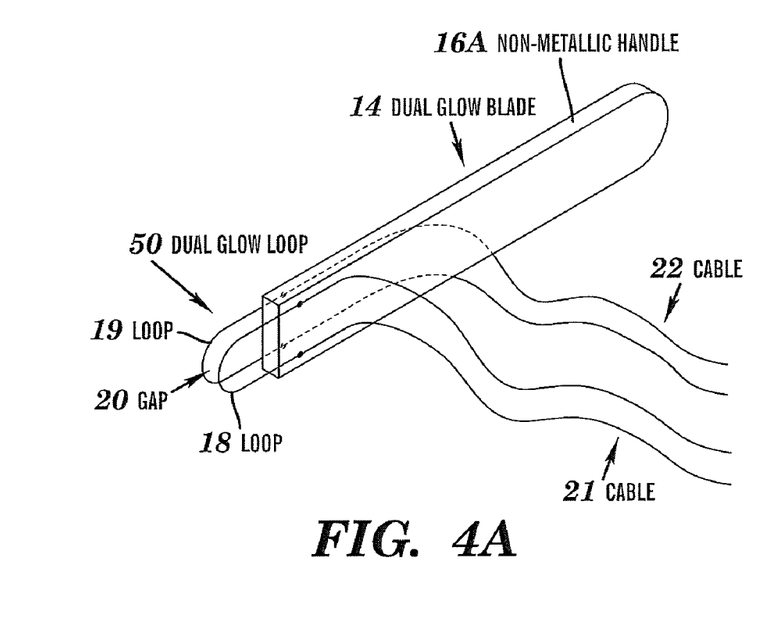
FIG. 4A depicts the dual glow blade of FIG. 2 in greater detail, in accordance with embodiments of the present invention.

FIG. 4A depicts the dual glow blade 14 of FIG. 2 in greater detail, in accordance with embodiments of the present invention. Cable 21 and 22 simultaneously provide both RF and loop power to the glow loops 18 and 19. A non-metallic handle 16A supports a dual loop assembly of dual glow loop 50, comprising glow loops 18 and 19 having a gap 20 therebetween. The glow loops 18 and 19 each have same geometrical and physical characteristics as that of the glow loop 6 of FIG. 3 described supra.

Figure 4B:
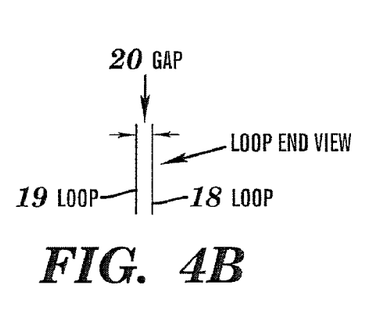
FIG. 4B is an isometric view of the two glow loops in the dual glow blade of FIG. 4A, in accordance with embodiments of the present invention.

FIG. 4B is an isometric view of the two glow loops 18 and 19 in the dual glow blade 14 of FIG. 4A, in accordance with embodiments of the present invention. FIG. 4B depicts the loops 18 and 19 in close proximity with the gap 20 between the glow loops 18 and 19. The gap size of the gap 20 may range from 0.001 to 0.050 inches (e.g., 0.005 inch). The cables 21 and 22 connect the glow loops 18 and 19 to the glow amplifier 5 and the glow amplifier 13, respectively, as shown in FIG. 2.

FIG. 9 depicts an alternative electrosurgical apparatus configured for differential operation with a dual glow blade for use with a patient, in accordance with embodiments of the present invention. The electrosurgical apparatus of FIG. 9 differs from the electrosurgical apparatus of FIGS. 2 and 6 in that: a commercial electrosurgical unit 50 of FIG. 9 replaces the RF generator 30 of FIGS. 2 and 6; and the electrosurgical adapters 53A and 53B of FIG. 9 replace the power supplies 31A and 31B, respectively, of FIGS. 2 and 6. In all other respects, the electrosurgical apparatus of FIG. 9 and the electrosurgical apparatus of FIGS. 2 and 6 are essentially the same electrosurgical apparatus with respect to structure and functionality.

The commercial electrosurgical unit 50 is the RF power portion of a conventional electrosurgical apparatus used in the prior art. The dual glow blade 14 (see FIG. 2) comprises the glow loops 18 and 19 and operates in conjunction with the electrosurgical adapters 53A and 53B. The commercial electrosurgical unit 50 receives AC power as shown and has a high voltage output 51 and a common output 52. The high voltage output 51 is electrically connected, via the electrosurgical adapter 53A, to glow loop 18 which contacts the patient tissue 32. The common output 52 is electrically connected, via the electrosurgical adapter 53B, to glow loop 19 which also contacts the patient tissue 32.

The electrosurgical adapter 53A, which converts AC power to a pulse train to provide power to the glow loop 18, comprises a pulse generator/amplifier 56A and an RF isolation transformer 55A. An operator power control 54A connects to the pulse generator/amplifier 56A and controls the power in the pulse train by varying pulse rate, duty cycle, or amplitude of the pulse train, which controls the temperature of the glow loop 18. The RF isolation transformer 55A allows power to be coupled from the pulse amplifier 56A to the glow loop 18 while providing a high impedance for any stray RF current flowing from the electrosurgical unit 50. The transformer 55A is wound with sufficient distance between primary and secondary coils to achieve the desired RF isolation and deliver the required power to be supplied to the glow loop 18. In one embodiment, the electrosurgical adapter 53A may be replaced by a battery such as a battery representing the loop power supply 31A of FIGS. 2 and 6, for use with the commercial electrosurgical unit 50. Power to the loop 18 is supplied via the secondary of the isolation transformer 55A.

The electrosurgical adapter 53B, which converts AC power to a pulse train to provide power to the glow loop 19, comprises a pulse generator/amplifier 56B and an RF isolation transformer 55B. An operator power control 54B connects to the pulse generator/amplifier 56A and controls the power in the pulse train by varying pulse rate, duty cycle, or amplitude of the pulse train, which controls the temperature of the glow loop 19. The RF isolation transformer 55B allows power to be coupled from the pulse amplifier 56B to the glow loop 19 while providing a high impedance for any stray RF current flowing from the electrosurgical unit 50. The transformer 55B is wound with sufficient distance between primary and secondary coils to achieve the required power to be supplied to the glow loop 19. In one embodiment, the electrosurgical adapter 53B may be replaced by a battery such as a battery representing the loop power supply 31A of FIGS. 2 and 6, for use with the commercial electrosurgical unit 50. Power to the loop 19 is supplied via the secondary of the isolation transformer 55B.

The output from the electrosurgical adapters 53A and 53B of FIG. 9 is analogous to the output from the loop power supplies 31A and 31B, respectively, of FIG. 2. In FIG. 2, the output of the loop power supplies 31A and 31B are electrically decoupled from the AC power source of the RF generator 30 (e.g., by use of a battery as a power source of the loop power supplies 31A and 31B), which prevents unwanted RF power from flowing from the RF generator 30 to the power source of the loop power supply 31. Similarly in FIG. 8, the output of the electrosurgical adapter 53 is electrically decoupled from its AC power source and hence the power source of the electrosurgical unit 50 due to the output of the electrosurgical adapter 53 being decoupled from by the RF isolation transformer 55, which prevents unwanted RF power from flowing from the electrosurgical adapter 53 to the power source of the electrosurgical adapter 53.

The dual glow blade may be used for rapid coagulation of tissue (without accompanying cutting of tissue) in order to stop bleeding immediately (e.g.; to stops uncontrolled bleeding of soldiers wounded in combat). In one embodiment for such coagulation applications, the glow loops 18 and 19 may be brushed along the surface of the tissue being coagulated (e.g., moved in a brushing-type motion in a direction that is about parallel to the surface of the tissue being coagulated; e.g., about in the direction 62 in FIG. 2). Successful coagulation of tissue (without accompanying cutting of tissue) will occur with output power from the RF generator in a range of 1.25 to 125 watts.

Thus the RF generator 30 and the loop power supplies 31A and 31B are configured to operate concurrently, while the glow loops 18 and 19 are heated to a glow, to supply both sufficient RF power and associated electrical current across the living tissue 32 for cutting and/or coagulating the living tissue 32 by the glow loops 18 and 19.

The inventor of the present invention has determined that the dual glow blade embodiment of the present invention may be beneficially employed in a non-glowing mode for the glow loops, as an improvement over conventional electrosurgical devices of the prior art, if the dual glow blade embodiment is implemented as described supra except that the glow loops 18 and 19 performs cutting and/or coagulation of tissue at a temperature below the minimum glow temperature of the material of the glow loops 18 and 19 (e.g., at a temperature in a range of about 300° F. to just below the minimum glow temperature). The minimum glow temperature of the material is defined as the minimum temperature at which the material glows (i.e., emits electromagnetic radiation in the visible portion of the electromagnetic spectrum).

EXAMPLE

The electrosurgical apparatus of the present invention is fully operational. The single loop glow blade whose glow loop is made of nickel chrome wire has been used to cut and cauterize living rat tissue while the glow loop was at a temperature of about 1652° F. In addition, the skin of a previously frozen pig's foot was cut and excised using the single glow blade The cutting was smooth and allowed for precise excision of unwanted tissue. When cutting, the single glow blade was moved across the target tissue similar to a conventional knife. In practice, however, some back and forth motion may be employed. In one embodiment, the loop may be placed over the tissue and its edge gently pressed against and into the tissue to create a cut.

It is also possible to undercut; i.e., to move the glow blade under the target tissue, where the blade may be shaped as required to first penetrate the target tissue, followed by cutting under the target tissue. Cutting along a curve is practical, since the glow blade may be easily bent by a user (e.g., a surgeon) to the required curvature While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. An electrosurgical apparatus for cutting and/or coagulating living tissue, comprising:
   at least one cutting probe having resistance material;
   a radio frequency (RF) generator; and
   a power supply for at least one cutting probe, the power supply configured to independently supply sufficient electrical current to heat the resistance material of the cutting probe to a glow wherein the cutting probe is ready and able to give off electrons,
   wherein the RF generator and the power supply are configured to operate concurrently, while at least one cutting probe is heated to said glow, to supply both sufficient RF power and associated electrical current across the living tissue for cutting and/or coagulating by at least one cutting probe, and
   wherein a first output of the RF generator is electrically coupled to at least one cutting probe.

2. The electrosurgical apparatus of claim 1, wherein the power supply includes a first power supply, and wherein there is no electrical current path from any output of the RF generator into the first power supply.

3. The electrosurgical apparatus of claim 1, wherein at least one cutting probe includes a single cutting probe, and wherein the power supply includes a first power supply.

4. The electrosurgical apparatus of claim 3,
   wherein the first output of the RF generator is electrically connected to both a first output of the first power supply and a first portion of the single cutting probe,
   wherein a second output of the first power supply is electrically connected to a remaining portion of the single cutting probe, and
   wherein a second output of the RF generator is adapted to be electrically connected to a patient pad which is in physical and electrical contact with the patient to facilitate electric current across the living tissue between the single cutting probe and the patient pad.

5. The electrosurgical apparatus of claim 1, wherein at least one cutting probe includes a first cutting probe and a second cutting probe, wherein the power supply includes a first power supply and a second power supply, wherein the first power supply is configured to supply electric current to the first cutting probe, and wherein the second power supply is configured to supply electric current to the second cutting probe.

6. The electrosurgical apparatus of claim 5,
wherein a first output of the RF generator is electrically connected to a first output of the first power supply,
wherein a second output of the RF generator is electrically connected to a second output of the second power supply,
wherein the first output and a second output of the first power supply are electrically connected to the first cutting probe,
wherein a first output and the second output of the second power supply are electrically connected to the second cutting probe, and
wherein the electrosurgical apparatus is configured to flow an electric current in the living tissue disposed between the first cutting probe and the second cutting probe.

7. The electrosurgical apparatus of claim 1, wherein the RF generator is configured to output power in a range of 1.25 watts to 125 watts.

8. The electrosurgical apparatus of claim 1, wherein the power supply is configured to receive power from a corresponding alternating current (AC) power source.

9. The electrosurgical apparatus of claim 1, wherein the power supply is configured to receive power from at least one battery.

10. The electrosurgical apparatus of claim 1, wherein the RF generator is a commercial electrosurgical generator.

11. A method for forming the electrosurgical apparatus of claim 1, said method comprising:
providing at least one cutting probe, the RF generator, and the power supply; and
electrically coupling a first output of the RF generator to at least one cutting probe.

12. A method, comprising using the electrosurgical apparatus of claim 1 to cut and/or coagulate the living tissue, said using the electrosurgical apparatus comprising:
applying electrical power to the RF generator to supply RF power for cutting and/or coagulating by at least one cutting probe;
applying electrical power to the power supply, resulting in a glowing of at least one cutting probe; and
during said applying electrical power to the RF generator and to the power supply, cutting and/or coagulating with the glowing of at least one cutting probe such that the RF generator and the power supply are operating concurrently to supply both sufficient RF power and associated electrical current across the living tissue for said cutting and/or coagulating by at least one cutting probe.

13. The method of claim 12, wherein said coagulating the living tissue comprises brushing the glowing at least one cutting probe along a surface of the living tissue being coagulated.

14. The method of claim 12, wherein the living tissue is living tissue of a human being.

15. The method of claim 12, wherein the living tissue is living tissue of a non-human mammal.

16. The electrosurgical apparatus of claim 1, wherein at least one cutting probe comprises a glow blade.

17. The electrosurgical apparatus of claim 1, wherein at least one cutting probe comprises a glow loop.

18. The electrosurgical apparatus of claim 1, wherein at least one cutting probe comprises a dual glow blade.

19. The electrosurgical apparatus of claim 1, wherein at least one cutting probe comprises a dual glow loop.

20. The electrosurgical apparatus of claim 1, wherein any cutting probe of at least one cutting probe comprises filament.

21. The electrosurgical apparatus of claim 1, wherein any cutting probe of at least one cutting probe comprises wire.

22. A method, comprising:
applying electrical power to an RF generator to supply RF power for cutting and/or coagulating by at least one cutting probe;
applying electrical power to a power supply, resulting in a glowing of at least one cutting probe; and
during said applying electrical power to the RF generator and to the power supply, cutting and/or coagulating with the glowing of at least one cutting probe such that the RF generator and the power supply are operating concurrently to supply both sufficient RF power and associated electrical current across living tissue for said cutting and/or coagulating by the at least one cutting probe.

23. The method of claim 22, said at least one cutting probe being a glowing loop of resistance wire.

24. The method of claim 22, said at least one cutting probe being a non-glowing loop of resistance wire.

25. The method of claim 22, wherein said cutting and/or coagulating the living tissue comprises brushing the at least one cutting probe along a surface of the living tissue being coagulated.

26. The method of claim 22, wherein the living tissue is living tissue of a human being.

27. The method of claim 22, wherein the living tissue is living tissue of a non-human mammal.

28. The method of claim 22, wherein said at least one cutting probe consists of one heated loop.

29. The method of claim 22, wherein said at least one cutting probe consists of two heated loops.

30. An electrosurgical apparatus comprising a cutting probe and a radio-frequency supply for applying a radio-frequency voltage between the cutting probe and living tissue to create an electric arc capable of vaporizing the tissue nearby the cutting probe and of coagulating any blood flow from the remaining tissue near the cutting probe, the improvement wherein the electrosurgical apparatus includes a supply for heating the cutting probe additional to that provided by the radio-frequency current in the electric arc, wherein the supply for heating the cutting probe is configured to supply sufficient electrical current to the cutting probe to heat the cutting probe to a glow wherein the cutting probe is ready and able to give off electrons, wherein both the supply for heating the cutting probe and the radio frequency supply are configured to operate concurrently, which additional heating is sufficient to reduce substantially the radio-frequency voltage necessary to sustain the electric arc reliably.

31. Electrosurgical apparatus with the improvement of claim 30 comprising:
the cutting probe, having resistance material;
the radio-frequency supply connected for applying the radio-frequency voltage between the cutting probe and the living tissue that is used to create the electric arc; and
the supply of heating for the cutting probe additional to that provided by the radio-frequency current in the electric arc, which supply of additional heating comprises
an electrical power supply other than said radio-frequency supply connected for causing current flow through the resistance material of cutting probe to provide the additional heating.

32. An electrosurgical apparatus with the improvement of claim 30 comprising:
a dual cutting probe, which includes first and second cutting probe; and
the radio-frequency supply connected for applying the radio-frequency voltage between the first and second cutting probes.

* * * * *